United States Patent [19]
Yang

[11] Patent Number: 5,504,961
[45] Date of Patent: Apr. 9, 1996

[54] ELECTRIC TOOTHBRUSH WITH DRIVE RELEASE

[76] Inventor: C. S. Yang, 6F. No. 41. Lane 228. Ho Ping East Road. Sec. 3., Taipei, Taiwan

[21] Appl. No.: 288,742

[22] Filed: Aug. 16, 1994

[51] Int. Cl.⁶ .................................................. A46B 13/02
[52] U.S. Cl. .................... 15/28; 15/22.1; 464/39; 464/37; 464/182; 192/110 R; 192/56.1; 433/118; 433/131; 74/98
[58] Field of Search .................. 15/28, 22.2, 22.4, 15/22.1; 464/37, 38, 39, 182; 192/56 R, 110 R; 433/118, 131, 114; 74/96, 98

[56] References Cited

U.S. PATENT DOCUMENTS

| | | | |
|---|---|---|---|
| 2,183,415 | 12/1939 | Thommies | 15/28 |
| 2,328,270 | 8/1943 | Greenberg | 15/22.2 |
| 2,766,470 | 10/1956 | Baker | 15/28 |
| 2,861,462 | 11/1958 | Hussar | 15/28 |
| 3,696,639 | 10/1972 | Gore et al. | 464/39 |
| 4,272,973 | 6/1981 | Fu-Tsai | 464/39 |
| 5,099,536 | 3/1992 | Hirabayashi | 15/28 |
| 5,311,633 | 5/1994 | Herzog et al. | 15/28 |

Primary Examiner—Gary K. Graham
Attorney, Agent, or Firm—Jones, Tullar & Cooper

[57] ABSTRACT

An electric toothbrush includes a handle section having a motor drive and a drive shaft coupled to the motor drive by a translating device, and a brush section having bristle assembly and a transmission shaft unit coupled to the drive shaft and driven by it to turn the bristle assembly back and forth alternatively, the transmission shaft unit consisting of a driving member, a connecting member, a driven member, and a compression spring, wherein the transmission shaft unit disengages from the drive shaft upon an overpressure to prevent damage to the bristles.

4 Claims, 4 Drawing Sheets

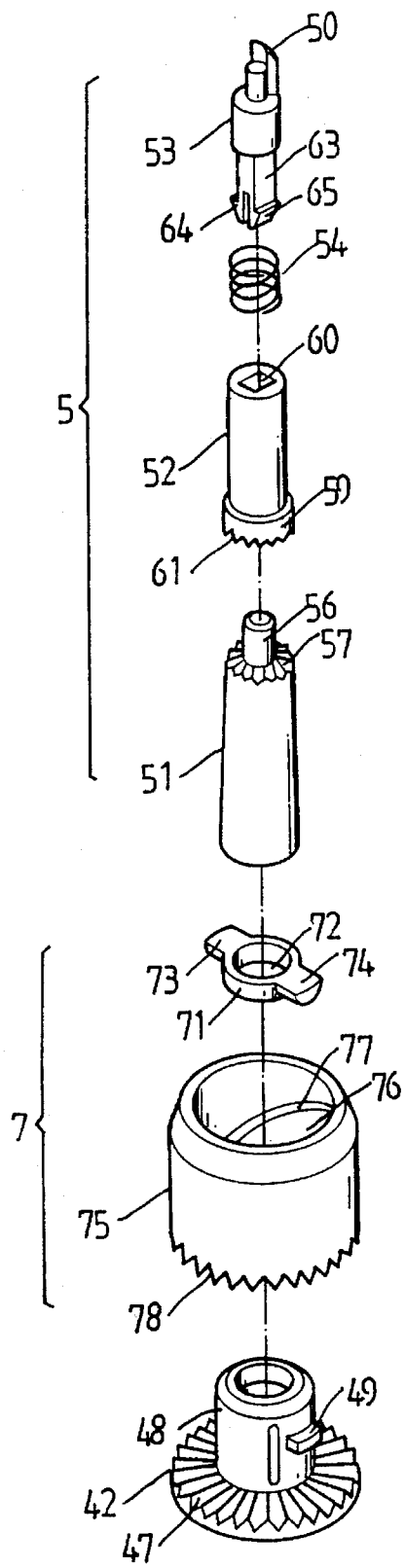
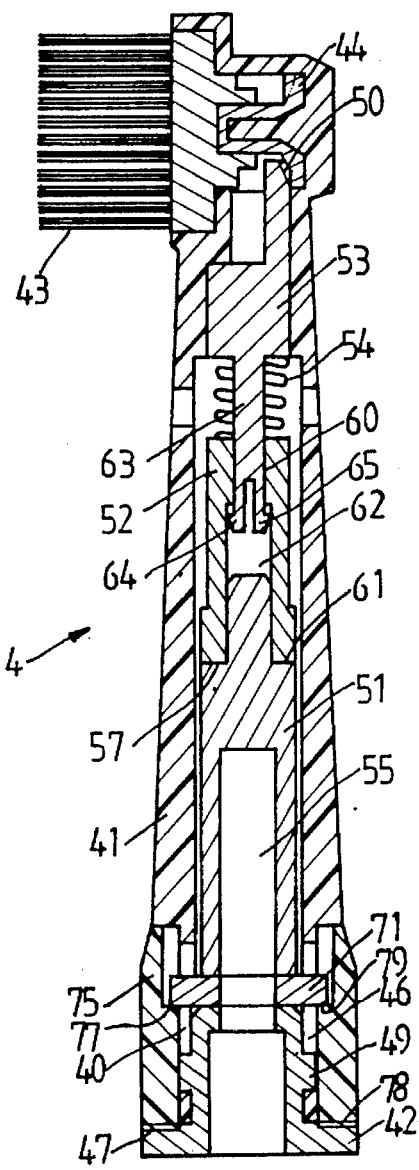
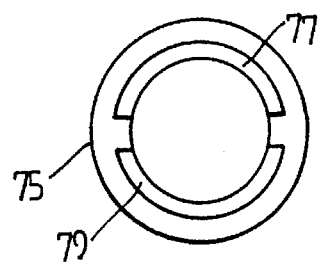
FIG. 5
FIG. 4
FIG. 6

ELECTRIC TOOTHBRUSH WITH DRIVE RELEASE

BACKGROUND OF THE INVENTION

The present invention relates to electric toothbrushes, and more particularly to an electric toothbrush which has an overload protection.

U.S. Pat. No. 5,289,604 discloses all electric toothbrush, as shown in FIG. 1. The electric toothbrush 10 comprises a handle section 1 and a brush section 2. The handle section 1 houses a battery 11, an electric motor 12, a drive shaft 13, and a translating device 14 for converting the continuous rotary motion of the electric motor 12 into a rotary motion reversing direction in alternating sequence for driving the drive shaft 13. The brush section 2 comprises a hollow mounting tube 23 receiving a brush shaft 22. Arranged at the end of the brush section 2 is a bristle supporting structure 21 for receiving bristles. The bristle supporting structure 21 has a bevel gear 24 meshed with a bevel gear 26 at the front end of the brush shaft 22. The mounting tube 23 and the brush shaft 22 are adapted to be connected to the handle section 1 by coupling means 25. When the bristles are damaged or worn away with use, the brush section 2 can be conveniently detached from the handle section 1 for a replacement. Locking structure is needed for locating the brush section relative to the handle section in an axial and a radial direction with respect to a longitudinal center line of the brush shaft. This structure of an electric toothbrush has certain drawbacks. Because the bristle supporting structure is turned back and forth at a speed of about 2,800 rpm., when an excessive pressure is applied to the bristles against the teeth, the teeth may be easily damaged. Therefore, electric toothbrush manufacturers commonly instruct the users not to apply much pressure on the bristles against the teeth. Furthermore, dentists do not recommend that children use electric toothbrushes because electric toothbrushes may damage growing children's teeth.

Because conventional electric toothbrushes lave no means to protect against overload, electric toothbrush users may apply a high enough pressure to the bristles against the teeth, causing damage to the teeth.

SUMMARY OF THE INVENTION

The present invention provides an electric toothbrush which eliminates the aforesaid problem. According to one aspect of the present invention, the brush shaft is comprised of a driving member engaged with the drive shaft of the handle section, a driven member engaged with the bristle supporting structure, a connecting member connected between the driving member and the driven member, and a compression spring connected between the connecting member and the driving member. When an excessive pressure is applied to the bristles against the teeth, the driving member of the brush shaft will be disengaged from the drive shaft, causing the drive shaft to run at idle.

According to another aspect of the present invention, a spring force adjustment device is provided to adjust the spring force of the compression spring so that the electric toothbrush can bear a different pressure for different users.

BRIEF DESCRIPTION OF THE DRAWINGS

FIG. 4 is a longitudinal view section to an enlarged scale of the brush unit of the electric toothbrush shown in FIG. 2;

FIG. 5 is an exploded view of the brush unit of FIG. 4; and

FIG. 6 is a bottom view of the adjustment ring shown in FIG. 5.

DETAILED DESCRIPTION OF THE PREFERRED EMBODIMENT

Figure 1:
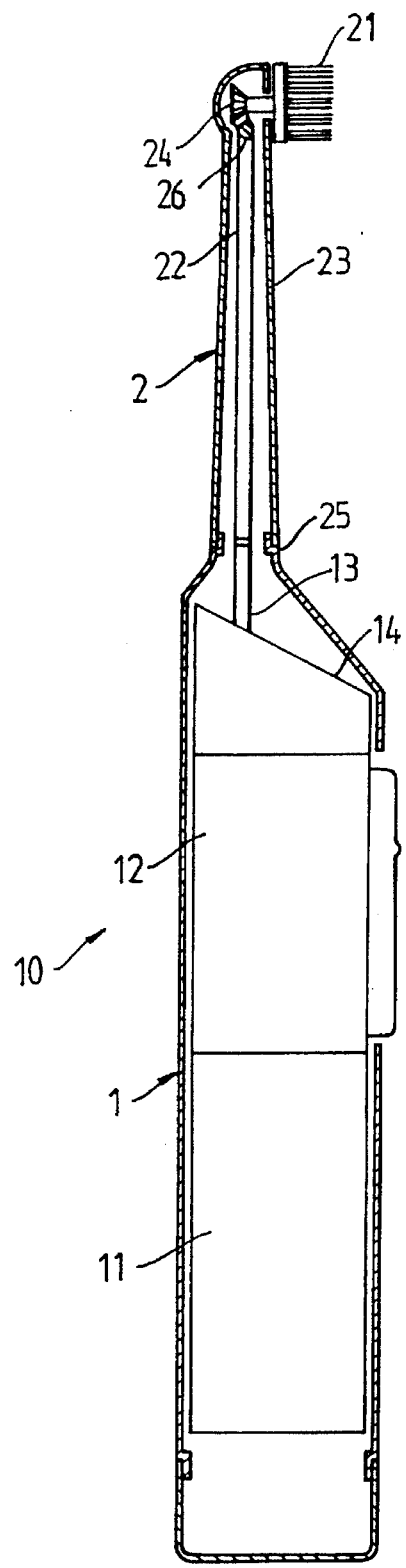
FIG. 1 is a longitudinal view in section of an electric toothbrush according to the prior art.
Figure 2:
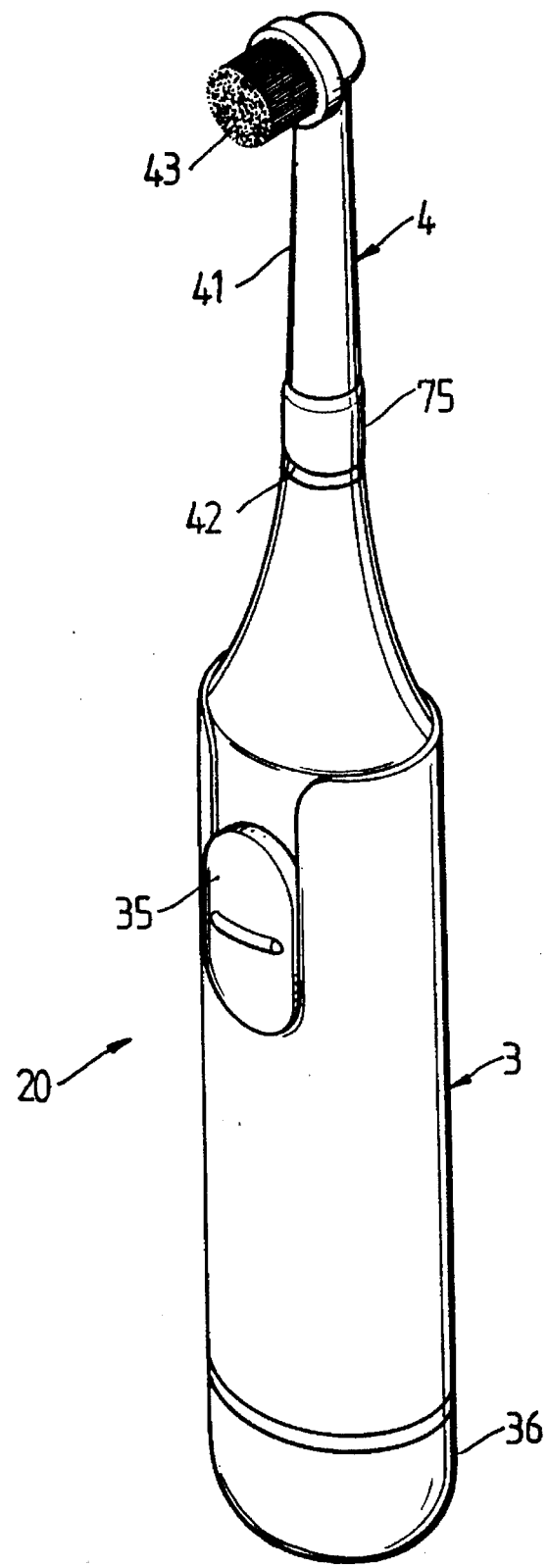
FIG. 2 is an elevational view of an electric toothbrush according to the present invention.
Figure 3:
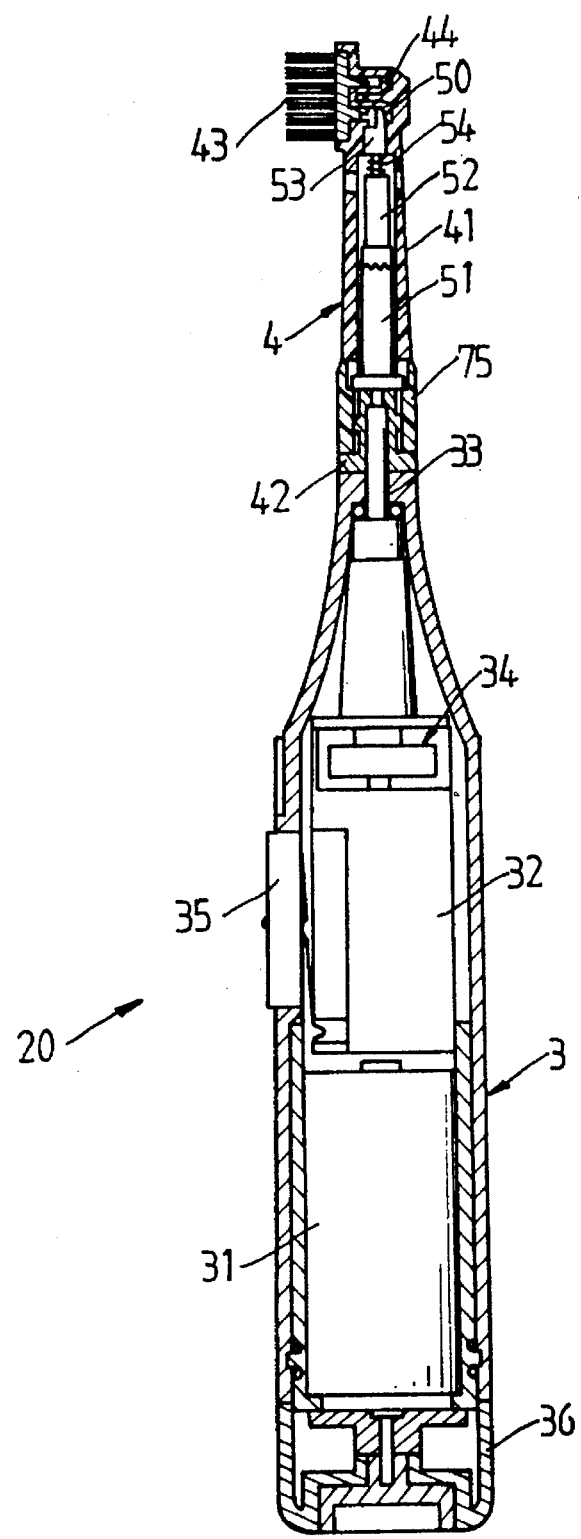
FIG. 3 is a longitudinal view in section of the electric toothbrush shown in FIG. 2.

Referring to FIGS. 2 and 3, an electric toothbrush 20, is generally comprised of a handle section 3 and a brush section 4. The handle section 3 houses two size "AA" batteries 31, an electric motor 32 and a translating device 34 for converting the continuous rotary motion of the electric motor 32 into an alternating rotary motion. A drive shaft 33 is coupled to the output end of the translating device 34 and extends out of one end, namely, the front end of the handle section 3. A slide switch 35 is mounted on the handle section 3 on the outside and moved to control the operation of the electric motor 32. A battery lid 36 is detachably covered on the open bottom end of the handle section 3. By opening the battery lid 36, the batteries 31 can be replaced. The brush section 4 comprises a housing or hollow mounting tube 41 receiving a transmission shaft unit 5. The hollow mounting tube 41 and the transmission shaft unit 5 are adapted to be connected to the handle section 3 by a coupling device 42. Therefore, when the bristles of the brush section 4 are damaged or worn away with use, the brush section 4 can be easily dismantled from the handle section 3 for a replacement. The transmission shaft unit 5 is coupled to the drive shaft 33. Arranged at the end of the brush section 4 remote from the handle section 3 is a bristle assembly 43. The bristle assembly 43 comprises a bevel gear 44 at the bottom meshed with a bevel gear 50 at the front end of the transmission shaft unit 5. Therefore, when the drive shaft 33 is alternately turned back and forth, the transmission shaft unit 5 is driven by the drive shaft 33 to turn bristle assembly 43 back and forth alternatively.

Referring to FIGS. 4 and 5, the transmission shaft unit 5 is comprised of a driving member 51, a connecting member 52, a driven member 53, and a compression spring 54. The driving member 51 has a plug hole 55 at one end, which receives the drive shaft 33, a front rod 56 at an opposite end, which inserts into the connecting member 52, a crown tooth form 57 disposed around the root of the front rod 56. The connecting member 52 comprises a crown tooth form 61 made on the bottom 59 thereof which meshes with the crown tooth form 57. Therefore, when the driving member 51 is turned back and forth by the drive shaft 33, the connecting member 52 is synchronously moved. The connecting member 52 further comprises a circular bottom hole 62, which receives the front rod 56 of the driving member 51, and a square top hole 60 longitudinally communicated with the circular bottom hole 62, which receives the split bottom rod 63 of the driven member 53. Arranged at the front end of the driven member 53 is the aforesaid bevel gear 50. The cross section of the split bottom rod 63 fits in the square top hole 60. Furthermore, the driven member 53 is molded from resilient plastics. Therefore, when time split bottom rod 63 of the driven member 53 is inserted into the square top hole 60 of the connecting member 52, the driven member 53 can then be turned back and forth by the connecting member 52.

The split bottom rod 63 has two hooked portions 64 and 65 at the bottom. When the split bottom rod 63 is inserted from time square top hole 60 into the circular bottom hole 62 and then pulled backwards, the hooked portions 64 and 65 become hooked on the peripheral edge around the boundary between the circular bottom hole 62 and the square top hole 60, and therefore the driven member 53 and the connecting member 52 are coupled together. The compression spring 54 is mounted around the split bottom rod 63 and stopped between the driven member 53 and the connecting member 52. The spring force of the compression spring 54 causes the crown tooth form 61 of the connecting member 52 to mesh constantly with the crown tooth form 57 of the driving member 51.

When the pressure applied to the bristle assembly 43 against the teeth surpasses the spring force of the compression spring 54, the crown tooth form 57 of the driving member 51 will jump relative to the crown tooth form 61 on the connecting member 52, causing the driving member 51 to run idle. Therefore, the bristles of the bristle assembly 43 are prohibited from being damaged by an overload. As the driving member 51 and the connecting member 52 are disengaged, the jumping of the crown tooth form 57 relative to the crown tooth form 61 will make a warning sound. When the pressure is reduced, the compression spring 54 forces the crown tooth form 61 of the coupling member 52 to mesh with the crown gear 57 of the driving member 51 again permitting the power of the rotary motion to be transmitted to the bristle assembly 43 again.

The specification of the compression spring 54 may be determined according to the application of the electric toothbrush 20. For example, a compression spring of small size may be used when the electric toothbrush 20 is designed for children; a larger size compression spring may be used when the electric toothbrush 20 is designed for adults.

Another feature of the present invention is the arrangement of a spring force adjustment device 7. As illustrated in FIGS. 4 and 5, the spring force adjustment device 7 comprises a sliding plate 71 and an adjustment ring 75. The sliding plate 71 is disposed between the coupling device 42 and the driving member 51, having a center through hole 72 for receiving the drive shaft 33, and two opposite horizontal wings 73 and 74 respectively extended out of two opposite longitudinal sliding slots 40 and 46 on the hollow tube 41 and driven by the adjustment ring 75 to move in the longitudinal direction. The adjustment ring 75 is mounted around the bottom end of the hollow tube 41 and stopped at the coupling device 42. The inner diameter of the adjustment ring 75 gradually reduces toward the bottom, having two curved surfaces 77 and 79 symmetrically disposed on the inside wall 76 thereof (see FIG. 6). The two opposite horizontal wings 73 and 74 of the sliding plate 71 are respectively stopped at the curved surfaces 77 and 79. Wheel the adjustment ring 75 is turned in one directions, the two opposite horizontal wings 73 and 74 or the sliding plate 71 are forced upwards along the longitudinal sliding slots 40 and 46 by the curved surfaces 77 and 79, causing the compression spring 54 to become relatively compressed. On the other hand, the compression spring 54 is relatively released when the adjustment ring 75 is turned in the reversed direction.

Referring to FIGS. 4 and 5 again, the adjustment ring 75 further comprises a crown tooth form 78 at the bottom releasably meshed with a crown tooth form 47 on the coupling device 42. The coupling device 42 comprises a tubular coupling portion 48 inserted into the hollow tube 41 from the bottom, and two locating blocks 45 and 49 raised from the tubular coupling portion 48 at two opposite sides and respectively engaged into the two longitudinal sliding slots 40 and 46 on the hollow tube 41.

What is claimed is:

1. An electric toothbrush comprising: a handle section including an electric motor drive providing a continuous rotary motion, a translating device connected to the electric motor drive for converting the continuous rotary motion of the electric motor drive into an alternating rotary motion, and a drive shaft coupled to the translating device; coupling means; a brush section including a transmission shaft unit coupled to the drive shaft and a housing for receiving the transmission shaft unit, the housing being detachably coupled to the handle section by the coupling means; and a bristle assembly turned alternatively back and forth by the drive shaft through the transmission shaft unit, the bristle assembly having a bevel gear; wherein the transmission shaft unit comprises:

an elongated driving member having a plug hole at one end, which receives the drive shaft, a front rod at the opposite end, and a crown tooth form between the two ends;

a longitudinally extending connecting member having a crown tooth form at one end thereof which releasably meshes with the crown tooth form of said driving member, a circular hole at the end having the crown tooth form, which receives the front rod of said driving member, and a square hole at the opposite end longitudinally communicated with said circular hole;

a driven member having a bevel gear at one end which meshes with the bevel gear on the bristle assembly and an opposite end terminating in a split rod which is inserted into said square hole and circular hole of said connecting member, said split rod having two opposite hooked portions hooked at an edge inside said connecting member between said square hole and said circular hole thereby preventing separation of said driven member from said connecting member; and a compression spring mounted around said split rod of said driven member and supported between said driven member and said connecting member.

2. The electric toothbrush of claim 1, further comprising: a spring force adjustment device for adjusting the spring force of said compression spring, said spring force adjustment device comprising a sliding plate and an adjustment ring, said sliding plate being disposed between said driving member of said transmission shaft unit and said coupling means and having a center through hole for receiving the drive shaft, said sliding plate also having two opposite wings respectively extending outwardly thereof, said adjustment ring being mounted around said housing of said brush section and releasably engaged with said coupling means and having two curved surfaces on its inside surface for supporting said wings of said sliding plate, said compression spring being relatively compressed when said adjustment ring is released from said coupling means and turned in one direction, said compression spring being relatively released when said adjustment is released from said coupling means and turned in the reversed direction.

3. The electric toothbrush of claim 2, wherein said coupling means comprises a tubular coupling portion inserted into said adjustment ring of said spring force adjustment device, and two locating blocks raised from said tubular coupling portion at two opposite sides and respectively engaged into the curved surfaces on the inside surface of said adjusting ring.

4. The electric toothbrush of claim 2, wherein said coupling means has a crown tooth form thereon, and said adjustment ring has a crown tooth form on a bottom thereof releasably meshed with the crown tooth form on said coupling means.

\* \* \* \* \*